(12) United States Patent
Feldhahn et al.

(10) Patent No.: US 9,625,065 B2
(45) Date of Patent: Apr. 18, 2017

(54) PLASTICS FOR MEDICAL TECHNICAL DEVICES

(75) Inventors: Karl-Andreas Feldhahn, Hamburg (DE); Gerd Schulz, Schenefeld (DE); Martin Eifler, Glückstadt (DE); Arnold Frerichs, Buxtehude (DE); Thomas Marx, Hamburg (DE); Elmar Vitt, Rotenburg (DE)

(73) Assignee: Loewenstein Medical Technology S.A., Luxembourg (LU)

( * ) Notice: Subject to any disclaimer, the term of this patent is extended or adjusted under 35 U.S.C. 154(b) by 2442 days.

(21) Appl. No.: 11/661,650

(22) PCT Filed: Jul. 22, 2005

(86) PCT No.: PCT/DE2005/001289
§ 371 (c)(1),
(2), (4) Date: Feb. 27, 2007

(87) PCT Pub. No.: WO2006/024253
PCT Pub. Date: Mar. 9, 2006

(65) Prior Publication Data
US 2008/0032119 A1 Feb. 7, 2008

(30) Foreign Application Priority Data

Sep. 3, 2004 (DE) .................. 10 2004 043 208
Mar. 18, 2005 (DE) .................. 10 2005 013 079
Jun. 14, 2005 (DE) .................. 10 2005 027 724

(51) Int. Cl.
| | | |
|---|---|---|
| *B29C 45/00* | (2006.01) | |
| *A61M 15/00* | (2006.01) | |
| *F16L 11/12* | (2006.01) | |
| *A61M 16/06* | (2006.01) | |
| *A61M 16/12* | (2006.01) | |
| *A61M 16/16* | (2006.01) | |

(52) U.S. Cl.
CPC .............. *F16L 11/12* (2013.01); *A61M 16/06* (2013.01); *A61M 16/0633* (2014.02); *A61M 16/0683* (2013.01); *A61M 16/12* (2013.01); *A61M 16/16* (2013.01); *A61M 2202/20* (2013.01); *A61M 2205/0238* (2013.01); *Y10T 428/26* (2015.01)

(58) Field of Classification Search
CPC .............. A61M 2202/20; A61M 16/06; A61M 16/0683; A61M 16/12; A61M 16/16; A61M 2016/0633; A61M 2202/0078; A61M 2205/0238; F16L 11/12
USPC ........... 128/205.25, 206.24, 206.21, 202.27, 128/203.12
See application file for complete search history.

(56) References Cited

U.S. PATENT DOCUMENTS

| | | | |
|---|---|---|---|
| 3,427,345 A | | 2/1969 | Holmen |
| 4,643,181 A | * | 2/1987 | Brown .................. 604/307 |
| 4,677,143 A | | 6/1987 | Laurin et al. |
| 4,911,974 A | | 3/1990 | Shimizu et al. |
| 4,985,277 A | | 1/1991 | Shimizu et al. |
| 5,327,940 A | * | 7/1994 | Presz, Jr. .................. 138/39 |
| 5,405,666 A | | 4/1995 | Brindle |
| 6,116,235 A | * | 9/2000 | Walters et al. .......... 128/200.24 |
| 6,467,483 B1 | * | 10/2002 | Kopacko et al. ........ 128/207.12 |
| 6,800,354 B2 | | 10/2004 | Baumann et al. |
| 6,977,094 B2 | | 12/2005 | Oles et al. |
| 7,144,473 B2 | | 12/2006 | Baecke |
| 7,703,456 B2 | | 4/2010 | Yahiaoui et al. |
| 2002/0142150 A1 | | 10/2002 | Baumann et al. |
| 2003/0124301 A1 | | 7/2003 | Oles et al. |
| 2003/0147932 A1 | | 8/2003 | Nun et al. |
| 2003/0154980 A1 | * | 8/2003 | Berthon-Jones et al. ...................... 128/204.18 |
| 2003/0221691 A1 | | 12/2003 | Biener et al. |
| 2004/0079374 A1 | * | 4/2004 | Thornton ................. 128/206.21 |
| 2004/0151930 A1 | * | 8/2004 | Rouns et al. ................ 428/500 |
| 2004/0157943 A1 | * | 8/2004 | Siegel .......................... 521/154 |
| 2004/0191420 A1 | * | 9/2004 | Rearick et al. ............... 427/384 |
| 2004/0261951 A1 | | 12/2004 | Baecke |
| 2005/0133035 A1 | | 6/2005 | Yahiaoui et al. |
| 2005/0167877 A1 | | 8/2005 | Nun et al. |
| 2006/0154048 A1 | | 7/2006 | Teranishi et al. |
| 2008/0032119 A1 | | 2/2008 | Feldhahn et al. |
| 2008/0078386 A1 | | 4/2008 | Feldhahn et al. |

FOREIGN PATENT DOCUMENTS

| | | |
|---|---|---|
| CA | 2260470 A1 | 7/1999 |
| CA | 2302118 A1 | 9/2000 |
| DE | 1748715 U | 7/1957 |
| DE | 44 04 680 | 8/1994 |
| DE | 44 25 278 | 1/1996 |
| DE | 10163800 A1 | 7/2003 |
| EP | 0298743 A2 | 1/1989 |
| EP | 0 828 715 | 3/1998 |
| EP | 0 933 380 | 8/1999 |
| EP | 0933388 A2 | 8/1999 |
| EP | 1040874 A2 | 10/2000 |
| EP | 1318228 A1 | 6/2003 |
| WO | 0249980 A1 | 6/2002 |
| WO | 03076169 A2 | 9/2003 |
| WO | 2004052640 A1 | 6/2004 |
| WO | 2005067753 A1 | 7/2005 |
| WO | 2006024253 A1 | 3/2006 |

\* cited by examiner

*Primary Examiner* — Audrea Buckley
(74) *Attorney, Agent, or Firm* — Abel Law Group, LLP

(57) ABSTRACT

The invention relates to a molded body, especially for parts, top shells, inner elements, accessories and components of devices, for molding materials, filling materials for medical technical devices and/or medical products. The inventive molded body is characterized by being in at least some sections germ-repellant. The invention also relates to a medical device which comprises at least one molded body according to the invention. The invention finally relates to a method for producing the inventive molded body.

67 Claims, 9 Drawing Sheets

PLASTICS FOR MEDICAL TECHNICAL DEVICES

Figure 1:
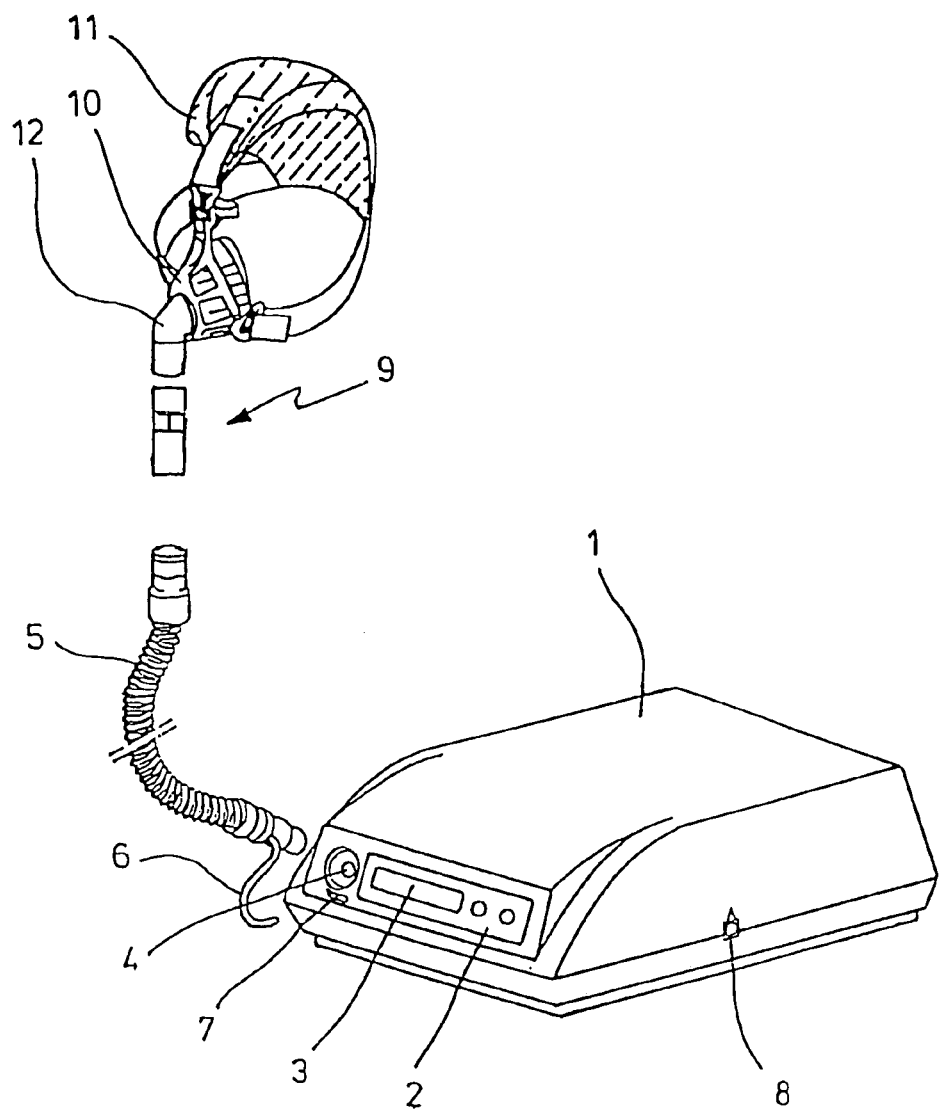

The invention concerns plastics for medical apparatus. The invention also concerns molded bodies for producing medical apparatus and methods for producing plastics and/or molded bodies in accordance with the invention.

Medical apparatuses can be a source of bacterial infection for the user. Possible sources are: the production, the service, the hospital, and the patient/user.

With regard to immunocompetent users, the risk of infection from apparatus is relatively low, but in immunosuppressed users, the situation is more problematic. Therefore, suitable measures must be taken, at least when a different patient starts to use the apparatus, to reduce or eliminate a possible bacterial infection. Most of the bacteria accumulate inside the apparatus. This is a problem especially in CPAP devices, ventilators, suction devices, and other types of medical apparatus.

Mechanical disinfection of CPAP devices, ventilators, suction devices, and other types of medical apparatus must be regarded as problematic, inefficient, and uneconomical when today's standard materials are used. The disassembly of the apparatus, spraying with surface disinfectants, placement of the individual parts in disinfectants, and subsequent reassembly of the apparatus is time-consuming and expensive. Moreover, the success of these measures is limited. All bacteria so far identified continue to live in the porous surfaces of the materials that are used and often successfully resist all attempts at mechanical disinfection. Therefore, in accordance with the state of the art, medical apparatus is regularly subjected to disinfection and/or autoclaving.

Successful disinfection can be achieved by formaldehyde fumigation in a sterilizer. In this method, the apparatus is fumigated in a sealed high-grade-steel chamber at a temperature of 45-50° C., a relative humidity of at least 85%, and a formaldehyde concentration of about 3,000 ppm. The chamber is then sufficiently ventilated. For safety reasons, a minimum ventilation time of 220 hours has been established.

The prerequisite for this type of disinfection is the use of aldehyde-resistant materials. It is also essential that the personnel in the disinfection unit receive technical training and training with respect to the application technology of the individual types of apparatus, so that the apparatus-specific characteristics of the individual types of apparatus can be considered. These measures are expensive and time-consuming.

Therefore, the objective of the invention is to simplify the hygienic treatment of medical apparatus.

In accordance with the invention, this objective is achieved by providing at least certain sections of the molded bodies with a surface coating.

A further objective of the invention is to design a medical apparatus in such a way that its functionality is improved.

In accordance with the invention, this objective is achieved by providing the apparatus with at least one component that has been furnished with a surface coating and/or by providing functional properties at the surface.

Another objective of the present invention is to improve a method of the aforementioned type in such a way that an embodiment is realized which is functional and at the same time inexpensive and capable of operating for extended periods of time.

In accordance with the invention, this objective is achieved by producing the molded body by plastic injection molding and then coating at least certain sections of the molded body.

The use of surface-coated components in medical apparatus basically allows much greater design latitude. The functional properties desired in a given situation can be provided by the surface coating, independently of the material of the substrate. The functional properties can be, for example, the aforementioned antiseptic properties, but they can also be related to antifriction properties, friction properties, surface shaping, or surface hardening.

The surface coating of the substrate is selected according to the predetermined functional property, and the base material of the substrate can be determined independently of the desired functional property of the surface and the mechanical or static boundary conditions. For example, it is possible, when high mechanical stresses are present, to provide a hard substrate with a softer surface coating or to furnish a soft and elastic substrate with an antiseptic functional surface. If necessary, the desired surface coatings are applied to the substrates with the use of suitable intermediate layers that serve as adhesion promoters.

The molded body of the invention is designed especially for apparatus parts, apparatus covers, apparatus internal parts, apparatus accessory parts, apparatus components, molding materials, filling materials for medical apparatus, and/or medical products and is characterized by the fact that the molded body is designed, at least in certain sections, to repel germ colonies, so that colonization by germs is prevented. The risk of infection, even in immunosuppressed users, is thus reduced in this surprisingly simple way.

In a preferred embodiment, the molded body is basically formed as an apparatus part, apparatus cover, apparatus internal part, apparatus accessory part, apparatus component, air humidifier, nebulizer, medication atomizer, ventilator, air-intake filter, sound absorber, air path in the apparatus, filter, ventilator mask, ventilator hose, emergency ventilator, suction device, suction hose, collecting container of a suction device, or as a defibrillator housing or housing part.

A molded body of this type for a medical apparatus is produced at least partly and/or in certain sections from plastic. In this regard, different plastics are often used. The plastics perform various functions and must be suited in the best possible way for the given function to be performed. The plastics used to make, for example, a ventilator are thus optimized for the specific purposes of the individual components, i.e., intake filter—ventilator—output filter—patient hose—filter—patient contact point.

All known plastics can be used as the plastics, e.g., polyethylenes, polypropylenes, polyvinyl chlorides, polystyrenes, polycarbonates, cellophanes, cellulose acetates, polyolefins, fluorocarbon resins Teflon), polyhydroxyethyl methacrylates (PHEMA)(Hydron), polymethyl methacrylates (PMMA), polysiloxanes, polyethers, polyesters, polyacetals, polyvinyls, polyethersilicones, polyurethanes, natural and synthetic rubber, silicone, latex, ABS resin, acrylic resins, triacetates, vinylides, and rayon.

In addition, it is possible to use all polymers that are suitable for the injection molding of injection-molded parts. Materials to be used for injection molding are preferably polymers or polymer blends that contain a polymer based on polycarbonates, polyoxymethylenes, poly(meth)acrylates, polyamides, polyvinyl chloride, polyethylenes, polypropylenes, linear or branched aliphatic polyalkenes, cyclic polyalkenes, polystyrenes, polyesters, polyethersulfones, polyacrylonitrile or polyalkylene terephthalates, polyvinylidene fluoride, polyhexafluoropropylene, polyperfluoropropylene oxide, polyfluoroalkyl acrylate, polyfluoroalkyl methacrylate, polyvinylperfluoroalkyl ether or other polymers of perfluoroalkoxy compounds, polyisobutene, poly(4-methylpentene-1), polynorbornenes as homopolymers or copolymers, or their mixtures. Especially preferred materials to be used for injection molding are polymers or polymer blends that contain a polymer based on polyethylene, polypropylene, polymethyl methacrylates, polystyrenes, polyesters, acrylonitrile-butadiene-styrene terpolymers (ABS), or polyvinylidene fluoride, such that the plastics can be used in pure form and/or as a mixture.

In addition to plastics, it is also possible to use metals and/or ceramic and/or glass, or any desired combinations of these materials, including combinations with the plastics listed above.

The molded body of the invention can be made at least partly of an antiseptic material. In this regard, antiseptic is understood to mean antibacterial, antimicrobial, antiviral, fungicidal, germicidal, or growth-inhibiting.

It is preferred, however, for at least some sections of the molded body to have a surface with antiseptic properties. In a preferred embodiment, at least some sections of the surface of the molded body are rendered antiseptic by reducing the surface adhesion. Bacteria and other microorganisms require water to adhere to a surface or to multiply on a surface, and water is not available on hydrophobic surfaces. The surface of the invention prevents the adherence of bacteria and other microorganisms and is thus bacteriophobic and/or antimicrobial.

One approach is reduction of the adhesion of proteins to surfaces. Since the cell membranes of microorganisms are also composed of protein constituents, reducing the adhesion of proteins reduces the attachment of microorganisms.

Polymers produced from one or more monomers that can be polymerized by free-radical polymerization are used for this purpose, such that these polymers have groups with permanent positive charge and groups that are capable of forming a bond on surfaces.

Alternatively, polymers that contain zwitterionic groups can be used. The zwitterionic group is usually an ammonium salt ester. The polymer that contains this group can be produced by free-radical polymerization of ethylenically unsaturated monomers together with a monomer that contains a zwitterionic group.

In addition, phosphorylcholine groups and nonionic ethoxylated and propoxylated surfactants can be used. Furthermore, biological polymers and synthetic surfactants can be used to reduce the adhesion of certain bacterial species by producing hydrophobic surfaces.

It is also possible to use antiadhesive surfaces produced by coating with hyaluron derivatives or polymers with repeating units with polar or polarizable, modulating, and hydrophobic fluoride-containing groups.

It is especially advantageous to use specially modified plastics which contain adhesion-lowering substances in an amount such that the adhesion of microorganisms on their surface is at least 50% lower than on the surfaces of unmodified plastics, and/or which contain biocidal substances in an amount such that at least 60% of the remaining microorganisms are killed within 24 hours.

In another embodiment, the surface of the molded body is rendered antiseptic by destroying microorganisms and/or inhibiting their growth. In this regard, microorganisms are organisms that belong to the following groups: bacteria, viruses, fungi, algae, plants, animals, protozoa, parasites, and metazoa. These microorganisms can be destroyed or their growth inhibited by the use of antibacterial, antimicrobial, antiviral, fungicidal, germicidal, or growth-inhibiting substances from all suitable chemical groups.

In another embodiment, the surface of the molded body contains biocides as active substances.

Biocides can be selected, for example, from the following groups: ciprofloxacin HCl (Bayer AG, Leverkusen), ciprofloxacin betaine, 2-n-octyl-4-isothiazolin-3-one, 2,3,5,6-tetrachloro-4-(methylsulfonyl)pyridine, N-trichloromethylthiophthalimide, chlorhexidine, triazines, methylthio-S-triazines, bromopol, dichlorophene, nitrapyrine, nickel dimethyldithiocarbamate, kasugamycin, octhilinone, furan carboxylic acid, oxytetracycline, probenazole, streptomycin, tecloftalam, copper sulfate and other copper preparations, long-chain bisphenol esters (U.S. Pat. No. 3,427,345; 3M), sodium fluoride in combination with dodecylamine or other organic amines, benzalkonium chloride, cetylpyridinium chloride, 4-chloro-2-(2,4-dichlorophenoxy)phenol (triclosan), oxiranyl triazolinethiones, complex or simple fluorides, such as $SnF_2$, $KZnF_3$, $ZnSnF_4$, and $Zn(SnF_3)_2$, potassium or zirconium hexafluorotitanate, N-oxides of saturated N-containing heterocyclic compounds substituted by quinolonecarboxylic acids or naphthyridonecarboxylic acids (EP 0 828 715 A1), monomer methacryloyloxydodecylpyridinium bromide (MDPB) in composite materials, 10,10-oxybisphenoxyarsine (OBPA), 2-n-octyl-4-isothiazoline-3-one (OIT), 2,3,5,6-tetrachloro-4-(methylsulfonyl)pyridine (TCMP), and N-trichloromethylthiophthalimide (NCMP), biguanides: —NH—C(NH)—NH—C(NH)—NH—, especially polyhexanide and chlorhexidine, where the biguanides are linked with a plastic polymer by the nitrogen atoms, polyoxyalkyldiamine biguanides, biguanide polymers cross-linked with isocyanates or epoxides (absorb biocidal silver salts), quaternary salt+antibiotic, poly N-halamine, 2-alkyl or 2-aralkyl benzisothiazolin-3-one derivatives, mixture of biocides in plasticizers with the simultaneous use of zinc oxide, plasticizers: adipic acid esters, phosphoric acid esters, phthalic acid esters, sebacic acid esters, sulfonic acid esters, trimellitic acid esters, and adipic acid polyesters, preferably phthalic acid esters (Unimoll™, DOP, DIDP, etc.) and adipic acid polyesters (Ultramoll™, etc.), especially combinations of Unimoll™ and Ultramoll™, Halo-Pure™, N-halamine, substances that release Hg, Sn, Pb, Bi, Od, Or, Ti, Ag, Cu, Zn, Ni, Pt, Sn, As Pb, Cd, Cr (MicroFree™ AMP, DuPont), for example, copper oxides or zinc silicates, but also the free metals. Silver halides, sulfates, and carbonates, organic silver salts, antibiotically active metal ions bound to ion exchangers: zeolites (A, X, Y, and T zeolites), mordenites, sodalites, analcime, chlinoptilolites, erionites, and amorphous aluminum silicates, nonzeolite support oxides from groups IIa, IIIa, IIb, IIIb of the periodic table: magnesium, calcium, strontium, barium, boron, aluminum, gallium, indium, zinc, scandium, yttrium and lanthanum, cerium, or mixtures thereof (DE 4425278), AgION antimicrobial (Ensinger GmbH, Nufringen): zeolite with large pore volumes binds silver ions. The zeolite releases the silver ions and binds cations from the environment in their place by ion-exchange processes; mixtures of silicon oxide, aluminum oxide, silver or silver oxide (especially for latex and silicone) (DE 4404680), pyrithione salt with metal, and homogeneous mixtures of calcium phosphate and silver. The aforementioned substances can also be used in any combinations.

Examples of suitable adhesion-reducing substances and methods for producing adhesion-reducing plastics or surfaces are those based on phosphorylcholine or phosphorylethanolamine, or those based on polyesters comprising units that are derived from glycerophosphorylcholine or glycerophosphorylethanolamine, and polyfunctional acids or their derivatives. The adhesion-reducing substances are introduced in amounts of about 0.05 to 50 parts by weight, preferably 0.1 to 20 parts by weight, per 100 parts by weight of the total compound or are applied as a surface coating.

The modified molded bodies for medical apparatus contain adhesion-reducing substances in such an amount that the adhesion of microorganisms on their surface is at least 50% lower than in the case of unmodified plastics, and/or they contain biocidal substances in such an amount that at least 60% of the remaining microorganisms are destroyed within 24 hours.

These modified molded bodies preferably have adhesion-reducing substances incorporated in them. In addition, their surfaces are modified by adhesion-reducing substances.

Furthermore, biocidal substances are preferably incorporated: silver, substances that release silver ions, copper, substances that release copper ions, zinc, or substances that release zinc ions.

To produce modified plastics, the adhesion-reducing and biocidal substances are introduced into the plastics.

In another, preferred refinement of the invention, the surface of the molded body contains silver and/or silver-containing compounds as the active substances.

The following table provides an overview of the properties of various silver active substances.

| Properties | Silver Zeolite | Silver Glass Ceramic | Nanosilver |
|---|---|---|---|
| Agent | $Ag^+$ | $Ag^+$ | $Ag^+$ |
| Sustained Release | $Ag^+$ | $Ag^+$ | $Ag^0$ |
| Matrix | zeolite | glass ceramic | — |
| Particle Size | 800-1000 nm | 800 nm | 5-50 nm |
| Impairment of Mechanical Stability | yes | yes | none |
| Photosensitivity and Darkening | yes | yes | none |
| Depot Inactivation (SH-Rg., halides) | strong | strong | none |
| Controllability of $Ag^+$ Release | poor | poor | very good |

For example, Ionpure™ is a nanosilver additive that imparts antibacterial and fungicidal properties to plastic products, synthetic fibers, composites, silicone products, paints, and coatings. The active components are silver ions in a glass matrix. In contrast to standard antibiotics, bacteria cannot develop resistance to silver ions. The incorporation of silver ions in a glass matrix prevents undesired reactions that occur with other additives based on silver ions and cause graying.

The necessary amount of Ionpure of 0.2-0.5% has no significant effects on the physical properties of the plastic products.

The antimicrobial effect lasts for years.

Alternatively, extremely small silver particles can be distributed in the spaces of the molecular chains of polymers. This does not adversely affect elasticity, the biocompatibility of the material is preserved, and the ability to destroy microorganisms lasts for many months.

If silver ions are used as the active substance of the antimicrobial plastics, a zeolite, which is a naturally occurring, extremely stable mineral, can be used as the support material of the silver ions. The crystal lattice of the zeolite has large pore volumes, so that large numbers of silver ions can be bound. The zeolite releases the silver ions and in their place binds cations in the environment, such as sodium, potassium, and calcium. This continuous release of the silver ions results in strong, long-lasting activity of the antimicrobial plastics. The active substance is resistant to chemicals with pH values of 3-10 and resistant to temperatures of up to 800° C. It was demonstrated that the compound is antibacterial and inhibits the growth of bacteria, yeasts, molds, and fungi in tests on more than 25 strains of microbes, including coliform bacteria, salmonellae, and staphylococci.

Another antibacterially active polymer based on nanoscale silver particles is "Polygiene™" (Perstorp, Sweden), a thermosetting molding compound with antiviral and antibacterial properties.

Silver particles can be produced in sizes down to 5 nanometers. This is accomplished by evaporating the noble metal in a vacuum and recondensing it on a surface. Particle sizes of 50-100 nm are normally produced in this way, but particle sizes of 5 nm can be achieved on flowing liquid films. The condensed particles are porous and are especially active due to their large surface.

Furthermore, the silver is highly pure and is not contaminated with other substances, as when it is produced by chemical production processes. The nanoparticles are incorporated in the polymer in finely divided form or are applied as a thin coating.

The nanosilver is distributed in the batch. In the finished product, nanosilver is wiped away from the surface by use. Silver is continuously brought to the surface by water. The antibacterial properties last for months.

In another preferred embodiment, the surface contains an antimicrobially active polymer as the active substance.

Nitrogen-functionalized and phosphorus-functionalized monomers are preferably used to produce the antimicrobial polymers, and these polymers are produced especially from one of the following monomers: 2-tert-butylaminoethyl methacrylate, 2-diethylaminoethyl methacrylate, 2-diethylaminomethyl methacrylate, 2-tert-butylaminoethyl acrylate, 3-dimethylaminopropyl acrylate, 2-diethylaminoethyl acrylate, dimethylaminopropyl acrylate, dimethylaminopropyl methacrylamide, diethylaminopropyl methacrylamide, acrylic acid 3-dimethylaminopropyl amide, 2-methacryloyloxyethyltrimethylammonium methosulfate, 2-diethylaminoethyl methacrylate, 2-methacryloyloxyethyltrimethylammonium chloride, <RTI 3-methacryloylaminopropyltrimethylammonium chloride, 2-methacryloyloxyethyltrimethylammonium chloride, 2-acryloyloxyethyl-4-benzoyldimethylammonium bromide, 2-methacryloyloxyethyl-4-benzoyldimethylammonium bromide, allyltriphenylphosphonium bromide, allyltriphenylphosphonium chloride, 2-acrylamido-2-methyl-1-propanesulfonic acid, 2-diethylaminoethyl vinyl ether, 3-aminopropyl vinyl ether.

The surface to be provided with antimicrobial properties can be totally or partially covered with the polymers.

It is possible to melt the antimicrobial polymer onto the surface and/or to apply such a small amount that, if necessary, the antimicrobial polymer retains its granular structure. The surface can be textured in this way.

In another preferred refinement of the invention, the surface of the molded body is rendered hydrophilic. The surfaces furnished with an antimicrobial finish can be rendered hydrophilic at or above the glass-transition temperature of the antimicrobial polymer by contact with water or acids, especially dilute organic or mineral acids. The enrichment with hydrophilic groups, which are often constituents of antimicrobial polymers, at the interface of the coated substrate, further promotes antimicrobial activity.

In another embodiment, the molded bodies have an antiseptic, photocatalytic surface. Photons penetrate the semiconductor titanium dioxide and may strike the surface at any time. If they encounter adherent organic material, then an electron exchange occurs, and the organic material is oxidized. Hydrogen peroxide ($H_2O_2$) arises as an intermediate product and intensifies the oxidizing effect. Fatty films, pathogenic microorganisms, and other organic contaminants are decomposed into water, carbon dioxide, and (if present) nitrogen, i.e. they are broken down by cold combustion. No change occurs at the surface of the titanium dioxide—it acts as a catalyst.

A photocatalytic coating, which consists only of a single nanocomposite, can be applied to all conceivable materials, including plastics, as easily as an ordinary coating. The coating is formed, for example, by the sol-gel process: organic coating structures initially become automatically concentrated over the substrate and form a strong chemical bond with the substrate material. Nanoparticles, e.g., of silicon, then line up to form a dense inorganic barrier, which, in addition, makes the whole coating resistant to abrasion. Billions of nanoparticles of titanium dioxide that become massed on the surface above the barrier are thus prevented from coming into contact with the organic layer, which they would destroy. Finally, the titanium particles, which are initially coated for the drying process, become oxidized to form the surface of the coating, so that the acivity of the uncovered titanium dioxide can take place.

Due to this aging process, the coating needs some time before it develops its full photocatalytic activity. The photocatalytic activity is significantly stronger than in previous coatings for two reasons: The photocatalytic titanium dioxide is present in the form of billions of nanoparticles. Due to the tiny size of the particles, the stimulated electrons and holes, during their movement through the material, strike the surface much more often, where they then become catalytically active. In addition, the total quantity of nanoparticles has a much larger surface all together than a continuous coating. This means that the active surface is also much greater.

To stimulate the self-cleaning effect, a small amount of coating material is also sufficient. A deposited organic fatty layer plays a supporting role in contamination. Such a layer not only contaminates the surface but also causes inorganic dust particles to adhere to the surface. This fatty layer is broken down photocatalytically, so that dust particles adhere to a far lesser extent. Since the titanium surface is hydrophilic as well, they adhere even less and are easily washed off, for example, with water.

In another embodiment, the molded body has an antiseptic and/or scratch-resistant surface.

Dirt-resistant coatings are highly resistant to abrasion. Due to their high abrasion resistance, these nonstick coatings open up many new types of applications that require not only the easy-to-clean property but also high mechanical and chemical stability. The coatings based on chemical nanotechnology are no longer formed by the previously used sol-gel process but rather by organic polymer chemistry with integration of ceramic nanoparticles.

Scratch-resistant surfaces combine, for example, the plastic polyurethane with nanotechnology. The outstanding properties of this versatile material, such as weather resistance, elasticity, and variation range, can thus be extended to scratch-resistant coatings with integrated ceramic nanoparticles. The invisible particles are modified at their surface in such a way that they can be chemically incorporated in the polyurethane network by a stirring process. The transparent surfaces open up a series of new applications for scratch-resistant surfaces.

In another embodiment, the molded body has an antiseptic, self-cleaning surface.

For self-cleaning surfaces, it is expected especially that the surfaces can be easily cleaned with water. The degree to which a drop of water wets a surface depends on the ratio of the energy used in increasing the surface area and the energy gained by adsorption.

On rough or hydrophobic surfaces, only a small amount of energy results from adsorption; the drop assumes an approximately spherical form and can "roll off". If a drop of this description then rolls over a particle of dirt on a rough surface, the surface of the drop relative to the air decreases, the adsorption energy increases, and the particle adheres to the drop and is carried along with it.

On the other hand, on a smooth surface the drop of water partially runs off and cannot entrain the particle, because the particle adheres more strongly to the smooth surface than to a rough surface due to the adhesive forces between the particle and the smooth surface.

In accordance with the invention, therefore, it is proposed that the surfaces be made rough and hydrophobic. In this regard, the surface can have an artificial surface texture that consists of elevations and depressions and has self-cleaning properties. The surface structures are preferably on the nm to μm scale. It is especially preferred for the surface structures to be spaced more or less evenly apart.

In addition, the surface structure can also have materials with antimicrobial properties. Furthermore, the surface can contain particles that are fixed on the surface by means of a matrix system.

It is especially preferred for the particles to consist of a mixture of hydrophobic particles and particles with antimicrobial properties.

The material with antimicrobial properties contains at least one antimicrobial polymer produced from at least one of the following monomers: 2-tert-butylaminoethyl methacrylate, 2-diethylaminoethyl methacrylate, 2-diethylaminomethyl methacrylate, 2-tert-butylaminoethyl acrylate, 3-dimethylaminopropyl acrylate, 2-diethylaminoethyl acrylate, 2-dimethylaminoethyl acrylate, dimethylaminopropyl methacrylamide, diethylaminopropyl methacrylamide, acrylic acid 3-dimethylaminopropyl amide, 2-methacryloyloxyethyltrimethylammonium methosulfate, 2-diethylaminoethyl methacrylate, 2-methacryloyloxyethyltrimethylammonium chloride, 3-methacryloylaminopropyltrimethylammonium chloride, 2-methacryloyloxyethyltrimethylammonium chloride, 2-acryloyloxyethyl-4-benzoyldimethylammonium bromide, 2-methacryloyloxyethyl-4-benzoyldimethylammonium bromide, 2-acrylamido-2-methyl-1-propanesulfonic acid, 2-diethylaminoethyl vinyl ether, or 3-aminopropyl vinyl ether.

In this regard, at least one surface of the molded body is made of a material which has self-cleaning properties and is selected from among polymers, such as polyamides, polyurethanes, polyether block amides, polyester amides, polyvinyl chloride, polyolefins, polysilicones, polysiloxanes, polymethyl methacrylates or polyterephthalates, metals, fibers, fabrics, glasses, or ceramics.

A material with antimicrobial properties is preferably used to produce the surface structures. In this regard, the surface structure, which consists of elevations or depressions, is preferably produced on the surface itself.

For this purpose, the surface structure is produced by applying and fixing particles on the surface. A matrix system is used to fix the particles. In this regard, the surface, the particles, and/or the matrix system can contain the antimicrobial material.

A polymer produced from at least one of the following monomers is used as the antimicrobial material: 2-tert-butylaminoethyl methacrylate, 2-diethylaminoethyl methacrylate, 2-diethylaminomethyl methacrylate, 2-tert-butylaminoethyl acrylate, 3-dimethylaminopropyl acrylate, 2-diethylaminoethyl acrylate, 2-dimethylaminoethyl acrylate, dimethylaminopropyl methacrylamide, diethylaminopropyl methacrylamide, acrylic acid 3-dimethylaminopropyl amide, 2-methacryloyloxyethyltrimethylammonium methosulfate, 2-diethylaminoethyl methacrylate, 2-methacryloyloxyethyltrimethylammonium chloride, 3-methacryloylaminopropyltrimethylammonium chloride, 2-methacryloyloxyethyltrimethylammonium chloride, 2-acryloyloxyethyl-4-benzoyldimethylammonium bromide, 2-methacryloyloxyethyl-4-benzoyldimethylammonium bromide, 2-acrylamido-2-methyl-1-propanesulfonic acid, 2-diethylaminoethyl vinyl ether, or 3-aminopropyl vinyl ether.

The particles that are used consist of a mixture of particles that contain at least one material selected from among silicates, doped silicates, minerals, metal oxides, silicic acids, or polymers that contain homopolymer particles or copolymer particles selected from the following group: 2-tert-butylaminoethyl methacrylate, 2-diethylaminoethyl methacrylate, 2-diethylaminomethyl methacrylate, 2-tert-butylaminoethyl acrylate, 3-dimethylaminopropyl acrylate, 2-diethylaminoethyl acrylate, 2-dimethylaminoethyl acrylate, dimethylaminopropyl methacrylamide, diethylaminopropyl methacrylamide, acrylic acid 3-dimethylaminopropyl amide, 2-methacryloyloxyethyltrimethylammonium methosulfate, 2-diethylaminoethyl methacrylate, 2-methacryloyloxyethyltrimethylammonium chloride, 3-methacryloylaminopropyltrimethylammonium chloride, 2-methacryloyloxyethyltrimethylammonium chloride, 2-acryloyloxyethyl-4-benzoyldimethylammonium bromide, 2-methacryloyloxyethyl-4-benzoyldimethylammonium bromide, 2-acrylamido-2-methyl-1-propanesulfonic acid, 2-diethylaminoethyl vinyl ether, or 3-aminopropyl vinyl ether.

In this regard, it is provided that the hydrophobic particles have a mean particle diameter of 0.05 to 30 nm.

However, the particles with antimicrobial properties have a diameter of 0.05 to 2,000 nm.

These particles form an irregular fine structure in the nanometer range on the surface.

In a preferred modification of the invention, the molded bodies have an antiseptic textured surface with regular and/or irregular elevations and/or depressions on the nm and/or μm scale.

In this regard, the surface has at least one firmly anchored layer of microparticles that form elevations. The elevations have a mean height of 20 nm to 25 μm and are spaced apart a mean distance of 20 nm to 25 μm. However, a mean height of 50 nm to 4 μm and/or a mean spacing distance of 50 nm to 4 μm is preferred.

In this regard, the microparticles are nanotextured microparticles that form a fine structure with elevations. The microparticles are selected from among particles of silicates, minerals, metal oxides, metal powders, silicic acids, pigments, metals, polymers, pyrogenic silicic acids, precipitated silicic acids, aluminum oxide, mixed-metal oxides, doped silicates, titanium dioxides, or powdered polymers, and preferably have hydrophobic properties.

The surface extrudate itself is a material selected from among polycarbonates, polyoxymethylenes, poly(meth)acrylates, polyamides, polyvinyl chloride, polyethylenes, polypropylenes, linear or branched aliphatic polyalkenes, cyclic polyalkenes, polystyrenes, polyesters, polyacrylonitrile or polyalkylene terephthalates, polyvinylidene fluoride, or other polymers of polyisobutene, poly(4-methylpentene-1), polynorbornenes as homopolymers or copolymers, a polymer based on polycarbonates, polyoxymethylenes, poly(meth)acrylates, polyamides, polyvinyl chloride, polyethylenes, polypropylenes, linear or branched aliphatic polyalkenes, cyclic polyalkenes, polystyrenes, polyesters, polyacrylonitrile or polyalkylene terephthalates, polyvinylidene fluoride, or other polymers of polyisobutene, poly(4-methylpentene-1), polynorbornenes as homopolymers or copolymers and their mixtures, as well as mixtures of the preceding materials.

Furthermore, the material has self-cleaning properties and elevations formed by microparticles. It is produced by pressing hydrophobic microparticles into the surface of the surface extrudate. The microparticles that are used have a mean particle diameter of 0.02 to 100 μm.

Textured surfaces with a low surface energy are also part of the invention.

It is well known that surfaces with a combination of microtexturing and low surface energy have interesting properties. The prior art according to EP 0 933 380 is that a surface energy of less than 20 mN/m is necessary for surfaces of this type.

Therefore, an object of the present invention is textured surfaces which have elevations with a mean height of 10 nm to 200 μm and a mean spacing distance of 10 nm to 200 μm and whose outer shape is described by a mathematical curve and/or function with symmetry with respect to a plane.

Examples of suitable materials are gold, titanium, silicon, carbon, quartz glass, lithium niobate, silicon nitride, hydroxylapatite, PMMA, silicones, epoxy resins, polydioxanone, polyamide, and polyimide. Surfaces can be characterized with respect to their wettability by measuring the surface energy. This quantity can be determined, for example, by measuring the wetting angle of various liquids on the smooth surface (D. K. Owens, R. C. Wendt, J. Appl. Polym. Sci. 13, 1741 (1969)) and is expressed in mN/m (millinewtons per meter). According to a determination made by Owens et al., smooth polytetrafluoroethylene surfaces have a surface energy of 19.1 mN/m.

An especially low surface energy is necessary especially when not only hydrophobic but also oleophobic behavior is required. This is the case especially with nonsolid oily contaminants (Lotus Effect™).

To produce such a surface, the textured, hydrophobic surface with elevations and depressions is treated with an additive that has a particle size of 0.0001 to 20 μm and an organic matrix that contains at least one thermoplastic, elastomeric, or thermosetting plastic.

This surface has self-cleaning properties and is scratch-resistant, abrasion-resistant, and/or stainable. Furthermore, the glass or plastic surface is antireflective.

Especially if the surface is provided with hydrophobic properties, it is difficult for it to be wet by water or aqueous solutions and thus has self-cleaning properties, since contaminants can be removed by moving water.

The device of the invention, which has surfaces that have liquid-repellent properties and surface texturing with elevations, is characterized by the fact that the surfaces are preferably plastic surfaces, in which microparticles are directly incorporated and are not bound by matrix systems or the like.

The materials of which the devices themselves preferably consist are polymers based on polycarbonates, polyoxymethylenes, poly(meth)acrylates, polyamides, polyvinyl chloride (PVC), polyethylenes, polypropylenes, polystyrenes, polyesters, polyethersulfones, linear or branched aliphatic polyalkenes, cyclic polyalkenes, polyacrylonitrile, or polyalkylene terephthalates, and their mixtures or copolymers. The injection-molded bodies consist more preferably of a material selected from among the following: polyvinylidene fluoride, polyhexafluoropropylene, polyperfluoropropylene oxide, polyfluoroalkyl acrylate, polyfluoroalkyl methacrylate, polyvinylperfluoroalkyl ether or other polymers of perfluoroalkoxy compounds, polyethylene, polypropylene, polyisobutene, poly(4-methylpentene-1), or polynorbornenes as homopolymers or copolymers. Most preferably, the injection-molded bodies contain one of the following as the material for the surface: polyethylene, polypropylene, polymethyl methacrylates, polystyrenes, polyesters, acrylonitrile-butadiene-styrene terpolymers (ABS), or polyvinylidene fluoride Microparticles, which form the elevations on the surface of the device, are preferably selected from among silicates, minerals, metal oxides, metal powders, silicic acids, pigments, or polymers, and more preferably from among pyrogenic silicic acids, precipitated silicic acids, aluminum oxide, silicon dioxide, doped silicates, pyrogenic silicates, or powdered polymers.

The surface of preferred microparticles has an irregular fine structure in the nanometer range, and the microparticles have a particle diameter of 0.02 to 100 μm, preferably 0.1 to 50 μm, and especially 0.1 to 10 μm. However, suitable microparticles can also have a diameter of less than 500 nm or can be agglomerates or aggregates built up from primary particles. These agglomerates or aggregates have a size of 0.2 to 100 μm.

Preferred microparticles are particles that contain at least one compound selected from among pyrogenic silicic acid, precipitated silicic acids, aluminum oxide, silicon dioxide, pyrogenic and/or doped silicates, or powdered polymers.

It can be advantageous for the microparticles to have hydrophobic properties. The hydrophobic properties can be based on the material properties of the materials themselves, which are present on the surfaces of the particles, or they can be produced by treating the particles with a suitable compound. The microparticles can have been furnished with hydrophobic properties before or after the application to or binding on the surface of the device or injection-molded part.

The surfaces with liquid-repellent properties are preferably hydrophobic, with the untextured material having a surface energy of less than 35 mN/m, and preferably a surface energy of 10-20 mN/m.

The invention also includes a method for producing plastic granules and powders.

If products made of polyolefins are to be lacquered, printed, coated, or adhesively bonded, it is necessary to pretreat the molded parts, since printing inks and adhesives do not adhere sufficiently well to the nonpolar surface of these plastics. Thermal or wet-chemical methods are customarily used. The desired oxidation of the surface can also be realized by an—electronic—plasma treatment.

A plasma method makes it possible to treat polyolefin granules and powders, so that a subsequent treatment of the parts can be eliminated. Very thin nanolayers, e.g., of polytetrafluoroethylene (PTFE, (Teflon)), can be deposited on various substrates by an HF CVD process. Different material surfaces can be provided with the desired functional properties in this way.

The chemical sol-gel process, which yields nanomaterials, is a variant of inorganic synthetic chemistry which until now has found little use in the development of materials. It uses liquid starting materials and a low-temperature process to produce inorganic or inorganic-organic materials with wide ranges of composition and structure.

The goal of using ceramics for the nanotexturing of surfaces is to alter the properties of known materials or to provide known materials with new functions, e.g., to produce columnar structures in the range of 20-300 nanometers on metal and plastics by embossing processes. This causes a change in interfacial properties. The formation of hemispherical structures with a radius of 250-350 nm on, for example, glass surfaces significantly reduces their reflection of light. This effect is based on the creation of a continuous transition between the surrounding air and the glass surface, which can be achieved in this way only by nanostructures.

A combination of microtexturing and nanotexturing can be used simply and easily to change the wetting of surfaces.

The solvent that contains the particles can be applied to the polymer surface, e.g., by spraying, by doctoring, by dropping, or by immersing the polymer surface in the solvent that contains the particles.

The method of the invention can be used to produce a self-cleaning polymer surface, which has an artificial, at least partially hydrophobic surface structure that consists of elevations and depressions formed by particles fixed on the polymer surface.

The particles can also be present in the form of aggregates or agglomerates. In this regard, according to DIN 53 206, aggregates are understood to be primary particles joined together along their surfaces or edges, while agglomerates are understood to be primary particles with point contact.

The structures described above can be produced, e.g., by an injection-molding process in combination with a conventional injection-molding die produced by the LIGA process. The LIGA process is a texturing process that is based on basic processes of x-ray lithography, electroforming, and molding. The process differs from micromechanics in that the structures are not produced in the base material by an etching process, but rather can be molded inexpensively by a die. In the present case, the LIGA process is used to produce the die.

Structures were molded in polypropylene with this die. The mold was then exposed for two minutes to UV radiation of 254 nm. Fluoroalkyl acrylate was thermally grafted onto the surfaces activated in this way. This procedure reduced the surface energy from about 28 mN/m to less than 15 mN/m.

In this process, it is not necessary to work antimicrobial polymers into the substrate, as is done, for example, in the compounding of molding compounds. Another advantage of the process is the economically efficient savings of antimicrobial polymers, which, e.g., in the case of compounding, remain in the matrix of the molding compound without effect. Furthermore, undesired changes in the physical properties of the substrates can be largely precluded in this way, since only a very thin layer on the surface of the substrate is changed. The method of the invention can be readily combined with other methods of surface finishing. It is possible, for example, after the thermally assisted application of the polymers, to carry out a hydrophilization step with water or acids.

The material properties of the various plastics are affected to only an insignificant extent. Characteristics such as the continuous use temperature, creep strength, and thermal and electrical insulation are preserved. The compound can be used under all conceivable conditions of production, processing, and use. It is used with semifinished products made of PEEK, PPSU, POM-C, and PET and with injection-molded parts, extruded sections, and calendered sheets.

Alternatively and/or in addition to the aforementioned properties, the molded bodies of the invention can have the following properties. It is also contemplated that a molded body of the invention can have several properties, at least in certain sections.

flame-retardant
low kinetic friction
anticorrosive
electrochemically active
low reflection
electrochromic
photochromic
piezoelectric
conductive
scratch-resistant
antireflective Alternatively and/or in addition to the aforementioned methods for producing molded bodies of the invention, the following processes can be used:

plasma process
laser process
sol-gel process
galvanic processes
production of nanostructures by self-organization
nanotexturing of materials and surfaces
vacuum evaporation (electron-beam evaporation)
vacuum evaporation (resistance crucible evaporation)
cathode sputtering
CVD processes (chemical vapor deposition)
PVD processes (physical vapor deposition
LIGA process
thermal oxidation
microelectroforming (hard alloy depositions)
injection molding of plastic microcomponents
vacuum coating
chemical electroplating
in-mold coating
precoating In addition, the invention includes a method for producing molded bodies of the invention. Advantageous embodiments of the method of the invention are specified in the dependent claims.

Specific embodiments of the invention are illustrated in the accompanying schematic drawings.

Figure 2:
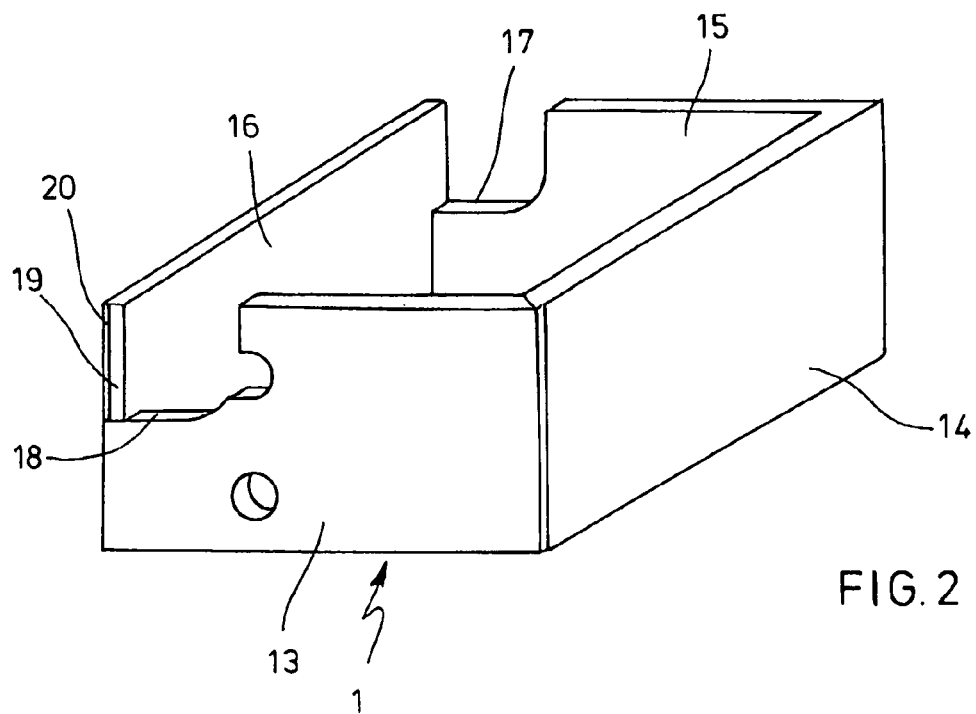
Figure 3:
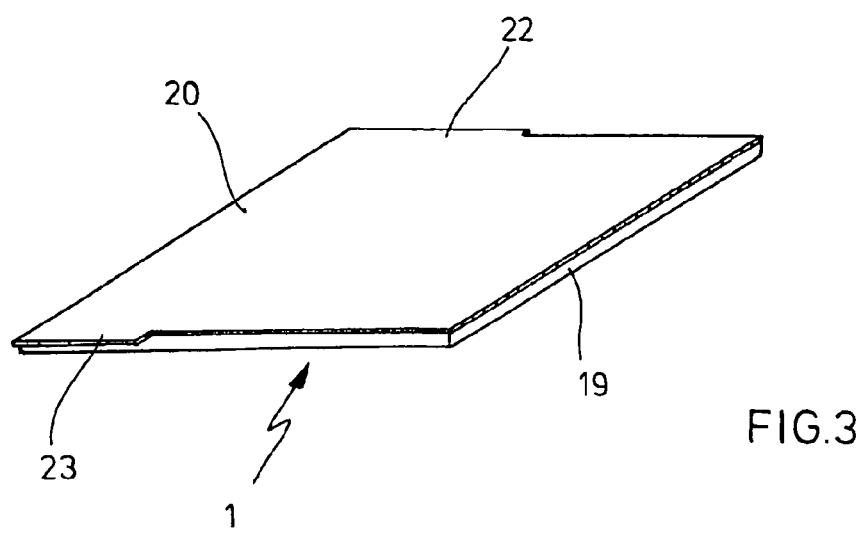
Figure 4:
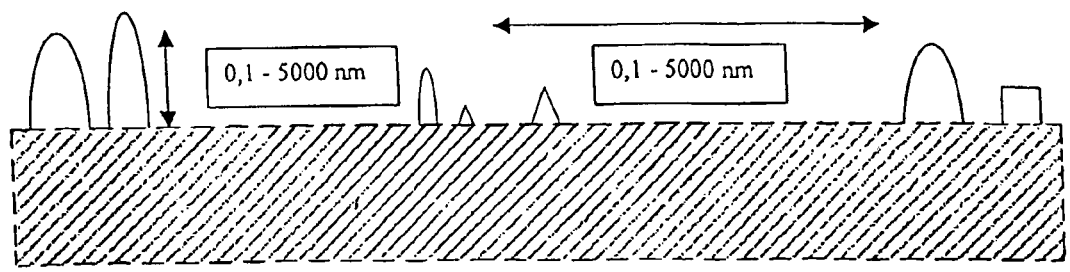
Figure 5:
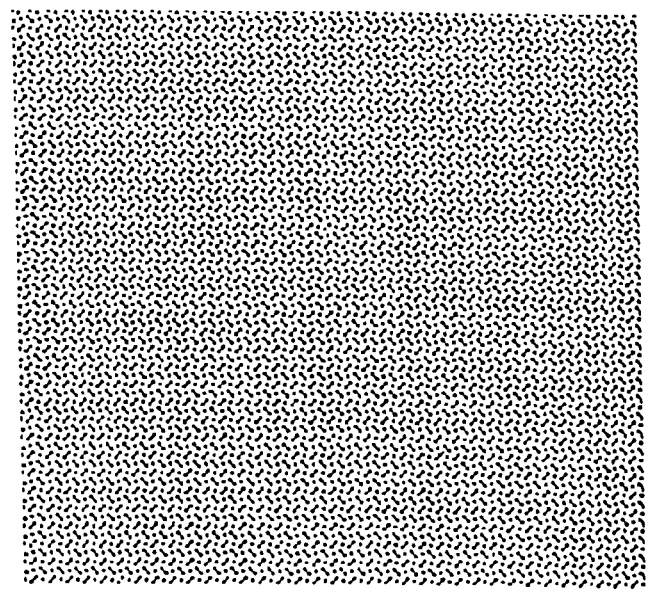
Figure 6:
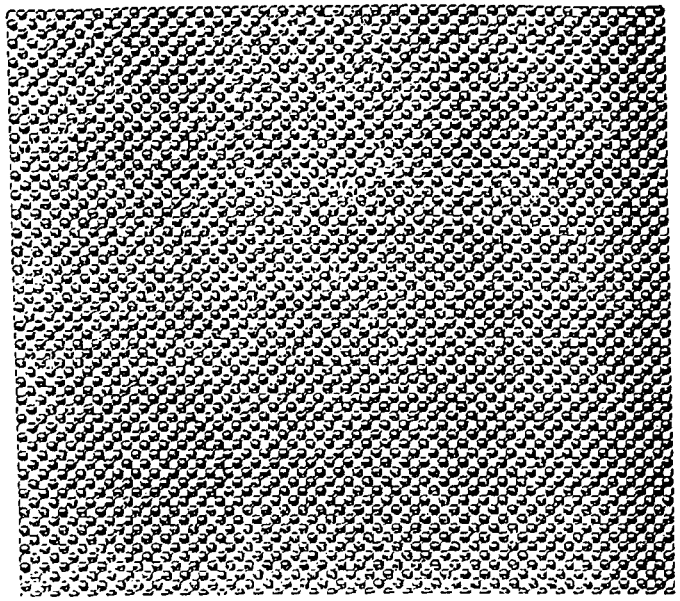
Figure 7:
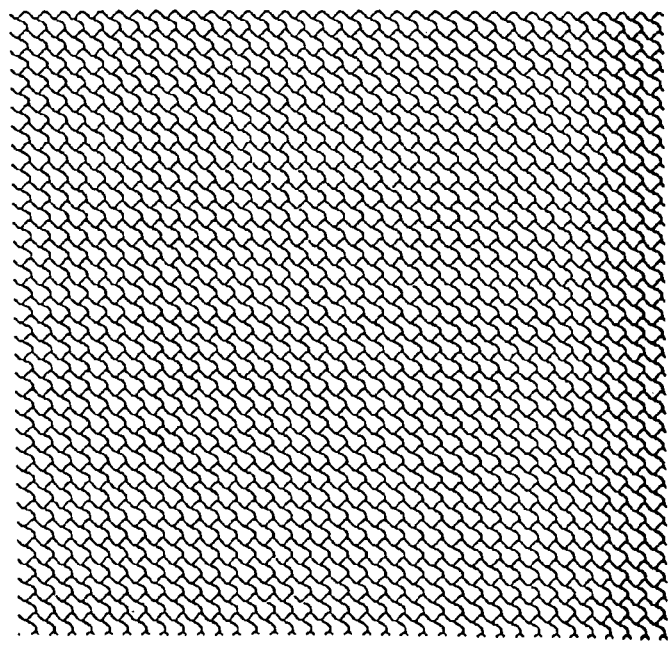
Figure 8:
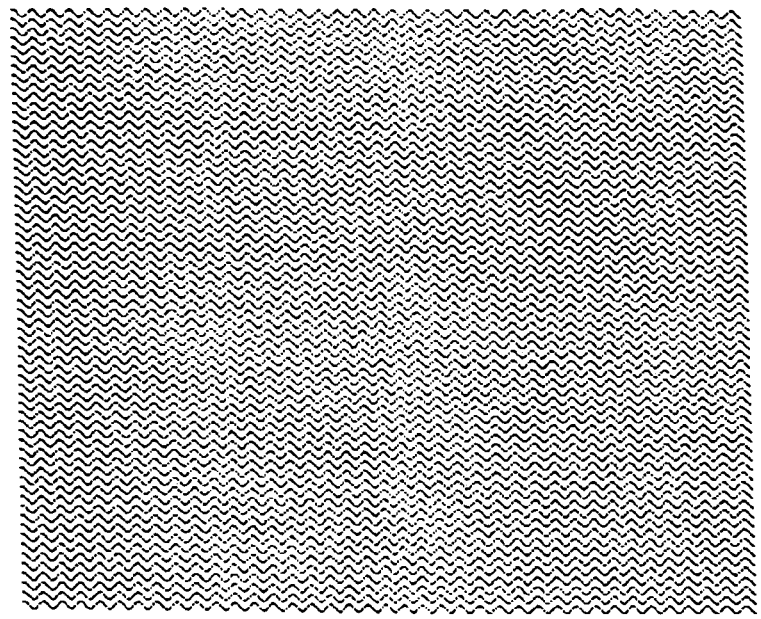
Figure 9:
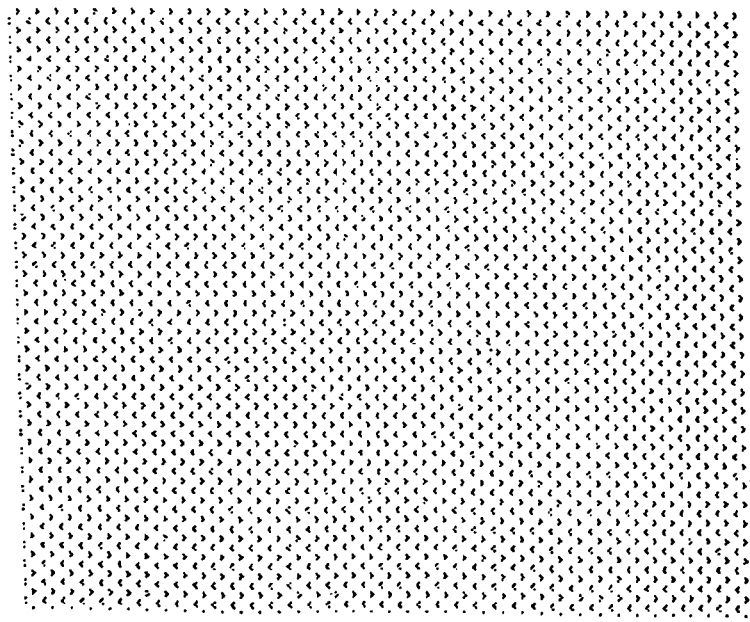
Figure 10:
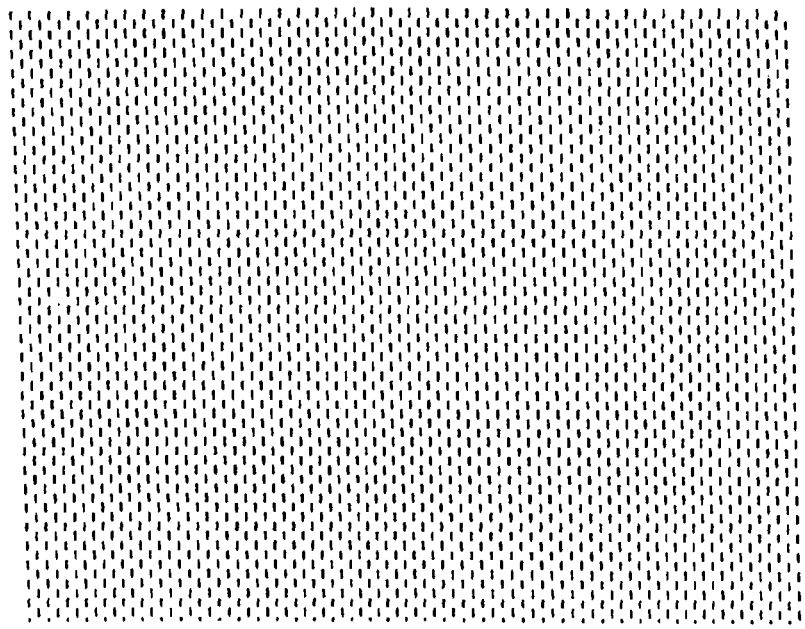
Figure 11:
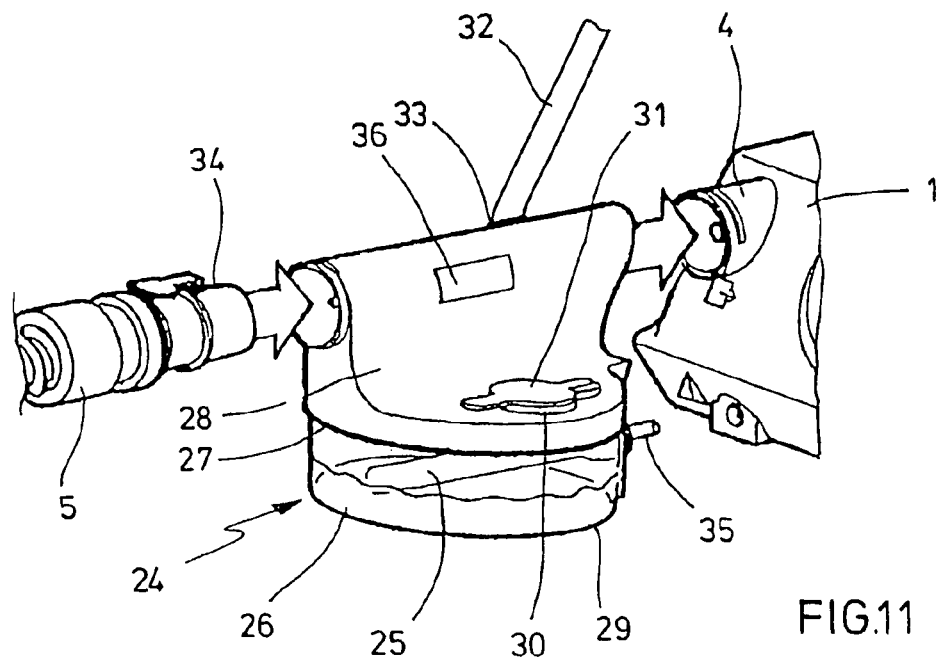
Figure 12:
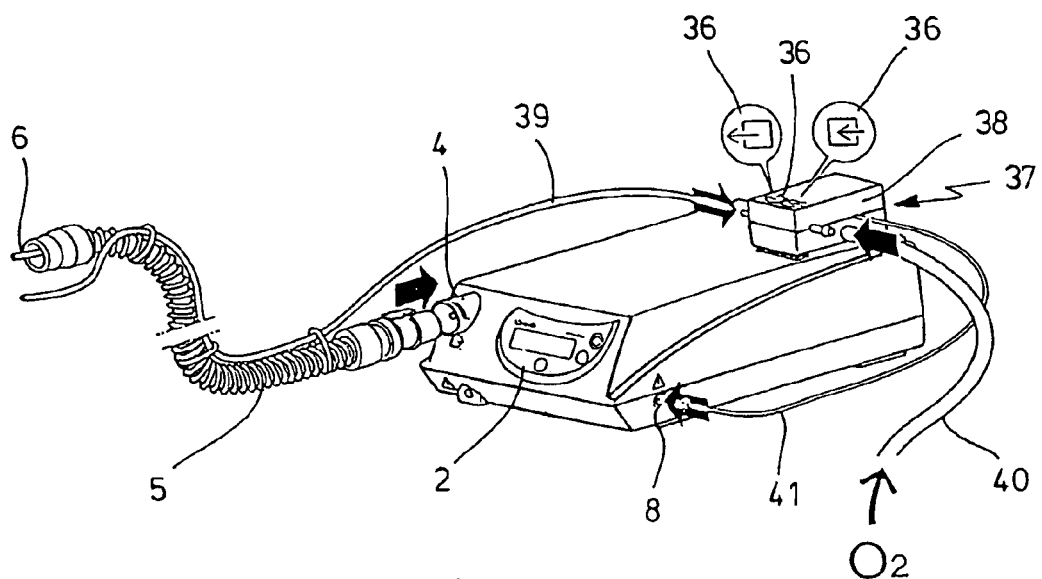
Figure 13:
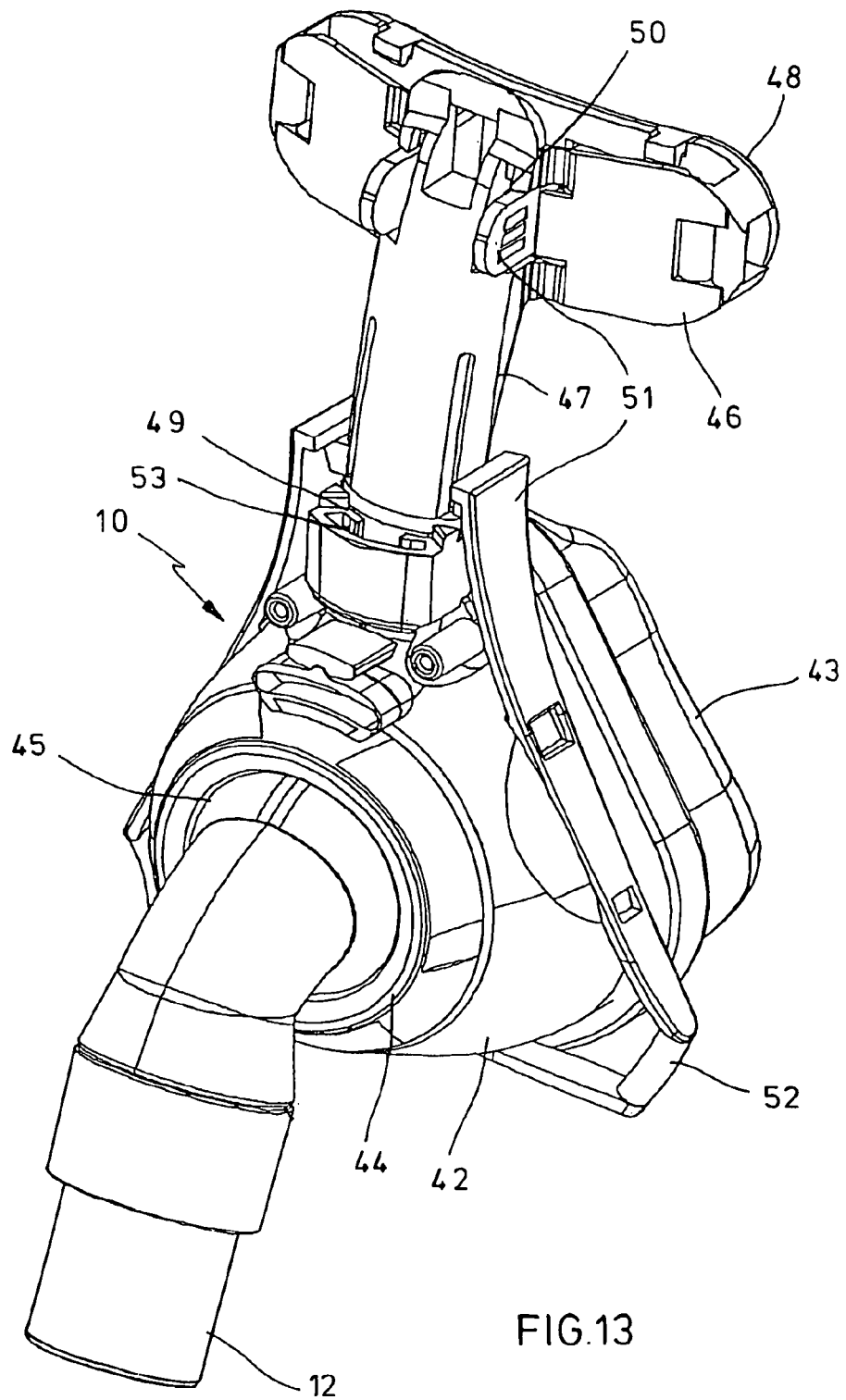
Figure 14:
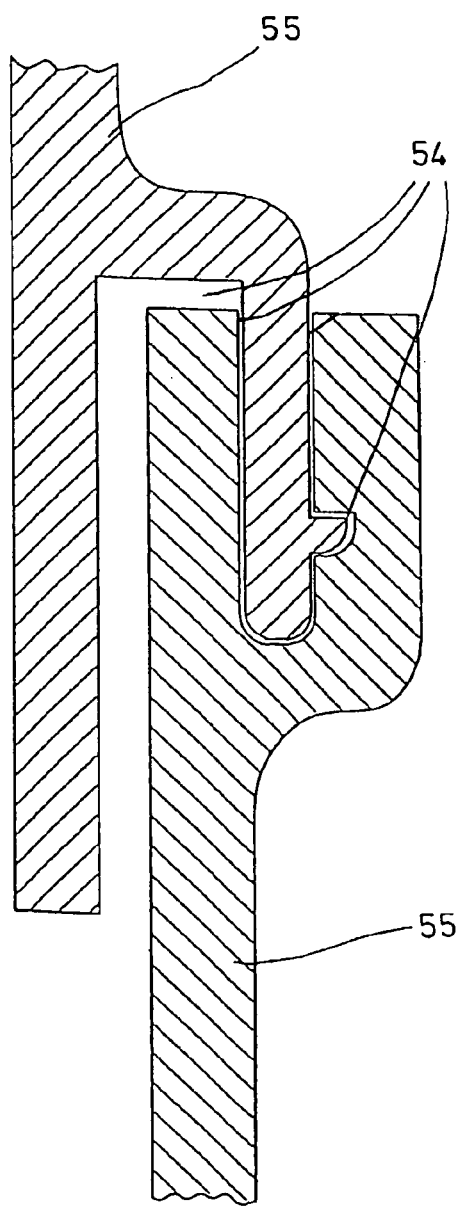

FIG. 1 shows a medical apparatus.
FIG. 2 shows a housing part of a medical apparatus.
FIG. 3 also shows a housing part of a medical apparatus.
FIG. 4 shows a surface profile.
FIGS. 5 to 10 show various types of surface topography.
FIG. 11 is a perspective drawing of a humidifier, which can be inserted between the ventilator and a ventilation hose.
FIG. 12 shows a ventilator with an oxygen supply valve for supplying an increased oxygen concentration.
FIG. 13 is a perspective drawing of a ventilator mask with a forehead support.
FIG. 14 is an enlarged partial cross-sectional view of two assembled components.

FIG. 1 shows the basic design of a ventilator. A respiratory gas pump is installed inside an apparatus housing 1, which has an operating panel 2 and a display 3. A connecting line 5 in the form of a hose is attached by a coupling 4. An additional pressure-measuring hose 6, which can be connected with the ventilator housing 1 by a pressure input connection 7, can run along the connecting hose 5. To allow data transmission, the ventilator housing 1 has an interface 8.

An expiratory device 9 is installed in an expanded area of the connecting line 5 that faces away from the apparatus housing 1. An expiratory valve can also be used.

FIG. 1 also shows a ventilation mask 10, which is designed as a nasal mask. The mask can be fastened on the patient's head by a head fastening device 11. A coupling device 12 is provided in the expanded region of the ventilator mask 10 that faces the connecting hose 5.

Each of the above functional elements is furnished with modified plastics to optimize it for its individual purpose. The mask 10, for example, is provided with a biocidal and nonfogging surface. The ventilator 1 is constructed from molded bodies formed as housing parts. The molded bodies are furnished with a scratch-resistant, biocidal, self-cleaning, and photocatalytic surface. The inside surface of the ventilator 1, especially the sound absorber (not show), is biocidal and/or self-cleaning. The intake filter is photocatalytic and biocidal.

FIG. 2 shows another apparatus housing 1, which consists of plate-like walls 13, 14, 15, 16. The apparatus housing 1 is provided with an inlet opening 17 and an outlet opening 18. The walls 13, 14, 15, 16 consist of a base material 19 covered with a surface coating 20. The apparatus housing 1 illustrated in FIG. 2 can be designed as a sound absorbing box for holding a fan or a compressor.

FIG. 3 shows a cover part 21 for the apparatus housing 1 illustrated in FIG. 2. The cover part 21 also consists of a base material 19 and a surface coating 20. The cover part 21 can have projections 22, 23 in the area of the inlet and outlet openings 17, 18 of the apparatus housing 1.

The surface coatings 20 can be produced by various methods, some of which have already been explained as examples. The surface coatings can be produced by introducing particles, as described above, but it is also possible to use vapor deposition techniques, lamination techniques, or plasma coating techniques. It is likewise possible to use the aforementioned methods for applying liquid coatings in pure form or diluted with solvents. Surface treatments, for example, those involving the use of mechanical means, laser beams, or electron beams, are also possible.

FIG. 4 shows a section of a surface profile of a modified molded body for a medical apparatus with elevations of various shapes, which have heights of 0.1 nm to 5,000 nm relative to the base. The distance between the individual elevations is likewise in the range of 0.1 to 5,000 nm.

These elevations are arranged in various forms on the surface to form regular structures.

In one embodiment, the invention comprises, for example, the following accessory parts that can be used for ventilation applications:

Humidifier (FIG. 10), $O_2$ valve (FIG. 12), head fastening device, patient interface (for example, mask, nasal pillows, tube), hose, filter, mounting, coupling, heater, interchangeable parts, pocket. It will now be explained how the invention contributes to improvement of the specified accessory parts.

Ventilators produce an air volume flow of up to 400 L per minute. The dimensions of a ventilator, the patient hose, and the patient interface are basically fixed within narrow limits. Therefore, the amount of power consumed in producing the air flow increases at a disproportionately high rate with increasing velocity of flow. At the same time, the generation of noise increases with increasing velocity of flow.

The reduction of noise generation, measured at a distance of 1 meter, can typically amount to at least 5% or at least 1 dB(A). In regard to the reduction of power consumption, it is intended especially that the reduction should be at least 2%. In another variant, the amount of time needed for a necessary cleaning should be reduced by at least 10%.

In regard to the occurrence of surface reflection, the functional property can consist in the production of an antireflective effect or an effect that lowers surface reflection at least for certain wavelengths and/or certain angles of incidence.

Therefore, in accordance with the invention, it is proposed that the frictional forces of the surfaces be reduced in order to save energy and/or limit noise generation. The reduced-resistance surfaces of the invention (see FIGS. 4 to 9 for examples) consist of microscopically small structures of the surface, for example, grooves, which are preferably aligned parallel to the direction of flow of the medium. Surfaces of this type are known in the natural world, for example, shark's skin. The surface structures are dimensioned in such a way that they act as a hydraulically smooth surface for the flowing medium. The reduced-resistance effect consists in hindrance of the turbulent components of the flow.

The surface structures are preferably spaced essentially equal distances apart. These essentially equal distances are in the range of 100 nm to 200 μm, and preferably in the range of 5 μm to 100 μm. It is especially preferred for the surfaces of the invention to have reduced resistance on the order of >1.0%.

In accordance with the invention, the air-conveying part of a ventilator and/or hose has, at least in certain sections, a textured surface with regular and/or irregular elevations and/or has a surface that reduces the friction of a flowing medium and/or has a flow-optimized surface.

To prevent the respiratory passages from becoming dry, the respiratory air is typically humidified. Since patients perceive warmed air to be pleasant, and since the air can hold more water vapor when it is heated, for example, by a heating element 25, a water supply tank that is used as a liquid reservoir 26 of the humidification system is typically heated indirectly and/or directly, for example, by the metallic base of the water supply tank or, for example, by means of an immersion heating element 25. A respiratory gas humidifier can be externally connected to a ventilator on the outside by a coupling 4 and/or it can be installed inside a ventilator. Due to hygienic requirements that must be met, it must be possible to remove the humidifier for cleaning and nevertheless to guarantee a sufficient seal from the water. The humidifier consists of an upper part 28, which serves essentially for conveying the air and also for connecting the ventilator 1 and the connecting hose 5, and a lower part 29 that holds the water supply. The upper part 28 has a liquid filling hole 30 with a closure 31.

A gas line 32, which is preferably designed as a pressure measurement line and/or oxygen supply line, can be arranged in the vicinity of the humidifier. The gas line is connected with the humidifier by a gas coupling 33. The humidifier can be coupled with a connecting hose 5 by a connecting adapter 34. Communication with the ventilator 1 can be realized by a plug connector 35 between the humidifier and the ventilator. A display 36 can be positioned near the humidifier.

A seal 27 is usually located between two detachable parts of the humidifier to prevent the escape of water and/or respiratory gas. Specifically, the inside of the humidifier must be regularly cleaned. According to the prior art, humidifiers are typically cleaned in a washing machine and, in addition, disinfected, if necessary, and care and cleaning are thus expensive.

In accordance with the invention, this disadvantage is eliminated by making the humidifier detachable and by providing at least certain sections of the humidifier with functional surfaces in accordance with the invention.

Surfaces are understood to be areas of the humidifier that are in contact with a medium, such as air or water. The surfaces in question can be inside surfaces of the humidifier, such as the inside surface of the water reservoir and/or the inside surface of the air-conveying part of the humidifier, or they can be the outside surfaces.

Contact points are areas of the humidifier and/or ventilator and/or connecting hose and/or patient interface and/or oxygen supply valve that are in contact with another molded body. In this regard, the contact points can be internal contact points of a molded body, such as the contact point between the lower part 29 and the upper part 28 of the humidifier, or they can be external contact points, such as the contact point between the humidifier and the ventilator.

Another example of an application will now be explained with reference to an oxygen supply valve 37. An oxygen supply valve 37 is a device for supplying oxygen to a user.

FIG. 12 is a perspective drawing of a ventilator 1 with a coupling 4 and an operating panel 2. A connecting hose 5 is connected by means of the coupling 4, and a pressure measurement line 6 passes through the connecting hose 5.

An oxygen line 39 is mounted on the outside of the connecting hose 5 and is connected with an oxygen supply valve 37. The supply valve 39 is connected to an oxygen source (not shown) by a supply line 40. A control line 41 connects the supply valve 39 with an interface 8 of the ventilator 1.

In the embodiment illustrated in FIG. 12, the supply valve 39 is mounted on the outside of the ventilator 1. However, it is also possible to integrate the supply valve inside the ventilator.

Preferably, at least some sections of the surface of the oxygen supply valve 37 are provided with antiseptic properties. The surfaces 38 of the oxygen supply valve are rendered antiseptic at least in some sections, for example, by reducing the surface adhesion. The surfaces 38 of the oxygen supply valve are rendered antiseptic at least in some sections, for example, by causing microorganisms to be destroyed and/or their growth to be inhibited. For example, the surface of the oxygen supply valve contains biocides. At least certain sections of the surface of the oxygen supply valve preferably contain silver and/or silver-containing compounds as the active substance. In another embodiment, the surface contains an antimicrobially active polymer as the active substance.

Alternatively and/or additionally, at least certain sections of the surface of the oxygen supply valve can be rendered hydrophilic. Alternatively, at least certain sections of the surface of the oxygen supply valve can be rendered antiseptic and/or photocatalytic and/or additionally hydrophilic. At least some sections of the oxygen supply valve can have a scratch-resistant surface. The oxygen supply valve preferably has a surface that is antiseptic, self-cleaning and/or hydrophilic and/or oleophobic and/or low-friction and/or conductive.

Another embodiment is explained below with reference to a head fastening device. As FIG. 1 shows, a ventilator mask 10 is typically attached to the head with a head fastening device 11. The head fastening device usually has one or more straps, which are connected with each other in the vicinity of their extension away from the mask and on the mask side make contact with the mask in at least two places. The head fastening device is usually fastened to the mask by contact mechanisms, such as clips and/or hooks and/or loops. The head fastening device can be supplemented by a chin strap.

Due to the constant contact with the patient, it must be possible to clean the head fastening device. Reliable removal of potential hygienically significant contamination must be possible. In prior art head fastening devices, which are typically washed in the washing machine, satisfactory hygienic cleaning is not guaranteed. In accordance with the invention, this disadvantage is eliminated by providing at least some sections of the surfaces of the head fastening device and/or of the surfaces of the contact mechanisms, such as clips and/or hooks and/or loops, with functional surfaces of the invention. Hereinafter, these surfaces will be referred to as surfaces of the head fastening device. Surfaces of the head fastening device can also be internal surfaces if, for example, coarse-pored fabric is used.

Preferably, at least some sections of the surface of the head fastening device are provided with antiseptic properties. The surfaces of the head fastening device are rendered antiseptic at least in some sections, for example, by reducing the surface adhesion. The surfaces of the head fastening device are rendered antiseptic at least in some sections, for example, by causing microorganisms to be destroyed and/or their growth to be inhibited. For example, the surface of the head fastening device contains biocides. At least certain sections of the surface of the head fastening device preferably contain silver and/or silver-containing compounds as the active substance. In another embodiment, the surface contains an antimicrobially active polymer as the active substance.

The head fastening device preferably has a surface that is antiseptic and/or self-cleaning and/or hydrophobic and/or oleophobic and/or photocatalytic and/or electrically conductive.

A patient interface will now be explained as the next example of an application. In the embodiment illustrated in FIG. 13, a patient interface is designed as a face mask 10. A mask is usually designed as a modular system and typically consists of the following components, which do not constitute a complete enumeration:

Body 42 of the mask and/or protruding edge 43 of the mask and/or expiratory system 44 and/or coupling element 12 and/or joint 45 and/or forehead support 46 and/or forehead support mount 47 and/or forehead cushion 48 and/or fastening device 52 for a head harness, securing ring, and/or release cord. The mask does not necessarily have to have all of the individual components for it to be functional.

The protruding edge 43 of the mask rests against the patient's face and provides the necessary seal. The body of the mask is connected with a coupling element 12 by means of a joint, and the coupling element 12 is connected with a ventilator hose. A forehead support 47 with a forehead cushion 48 is used to ensure reliable positioning of the ventilator mask on the patient's head. The forehead support is connected with the body of the mask by a mount 53.

The mask is adjusted on the patient by a coarse adjustment device 49 and a fine adjustment device 50 for the forehead support. The fine adjustment can be made, for example, by means of fine catches on the forehead support or on the forehead cushion. The coarse adjustment can be made, for example, by changing the position of the forehead support in the mount 53. For example, using the coarse adjustment, the patient moves the forehead support into the desired position and fixes the forehead support in the selected position with the use of the fine adjustment on the forehead cushion.

Complex swiveling or sliding mechanisms are also used for adjustment. Each of the adjustment mechanisms has operating surfaces 51 for the user. The components of the mask can be moved relative to each other by slight mechanical action of a user in the area of the operating surfaces. If the ventilator mask is used without a forehead support, a blind plug can be inserted in the plug connection, or an adapter can be used, which allows coupling with the head harness. The forehead cushion preferably can be detached from the forehead support. This allows easy replacement and/or separate cleaning.

The protruding edge of the mask can typically be detached from the body of the mask. The protruding edge of the mask is attached to the body of the mask, for example, by notches, webs, thickened sections, or grooves.

A release element can be mounted in the area of the body of the mask to allow the patient to break the connection between the ventilator hose and the ventilator mask with a single pull.

Various other patient interfaces can be used as alternatives to a mask. The following are named as examples: nasal pillows, tubes, tracheostoma, catheter.

An important requirement for patient interfaces is that it must be possible to clean them simply and effectively. For this reason, the surfaces of the invention are used in the area of the mask. Hereinafter, masks and all mask components, as well as other patient interfaces, such as nasal pillows, will be combined, for the sake of simplicity, under the term patient interfaces.

Preferably, at least some sections of the surface of the patient interfaces are provided with antiseptic properties. The surfaces of the patient interfaces are rendered antiseptic at least in some sections, for example, by reducing the surface adhesion. The surfaces of the patient interfaces are rendered antiseptic at least in some sections, for example, by causing microorganisms to be destroyed and/or their growth to be inhibited. For example, the surfaces of the patient interfaces contain biocides. At least certain sections of the surfaces of the patient interfaces preferably contain silver and/or silver-containing compounds as the active substance. In another embodiment, the surface contains an antimicrobially active polymer as the active substance. It is especially preferred for the operating surfaces to be biocidal and/or antiseptic.

At least certain sections of the patient interfaces preferably have a surface that is antiseptic and/or self-cleaning and/or hydrophobic and/or oleophobic and/or photocatalytic and/or scratch-resistant and/or nonfogging and/or nonirritating to the skin and/or low-friction and/or electrically conductive.

The projecting edge of the mask and/or the forehead cushion and/or nasal pillows are preferably antiseptic and/or self-cleaning and/or nonirritating to the skin and/or hydrophobic and/or oleophobic.

On its side facing the patient, the body of the mask is preferably antiseptic and/or self-cleaning and/or hydrophobic and/or oleophobic and/or photocatalytic and/or scratch-resistant and/or nonfogging and/or nonirritating to the skin. On its side facing away from the patient, the body of the mask is preferably antiseptic and/or self-cleaning and/or hydrophobic and/or oleophobic and/or photocatalytic and/or scratch-resistant. It is proposed especially that notches, webs, thickened sections, or grooves in the area of patient interfaces be provided with antiseptic and/or self-cleaning and/or hydrophobic and/or oleophobic and/or photocatalytic and/or scratch-resistant properties.

It is also proposed that points of contact of the individual components with each other and/or points of contact with the patient be provided with antiseptic and/or self-cleaning and/or hydrophobic and/or oleophobic properties.

It is especially preferred that the area near the side of the patient interface that faces the air flow be furnished with suitable smooth plastics and/or lacquered surfaces and/or coated plastics and/or surfaces with texturing on the nanometer to micrometer scale in such a way that reduced friction can be realized.

The invention can also be used together with a filter. Especially in ventilators but also in other types of medical apparatus, filters are used, mainly in the air intake area, to retain particulates, dust particles, and microorganisms. The filters are intended to prevent contamination of the apparatus and contamination of the patient. Alternatively and/or additionally, filters are used in the area between the apparatus and the patient or user, especially to avoid hygienic contamination. The filters usually take the form of replaceable plug-in filters. So-called combination filters are also used, which can be designed, for example, as coarse filters and fine filters. If a filter is not regularly cleaned and/or replaced, retained particulates, dust particles, and microorganisms can increase the flow resistance of the filter, which causes the efficiency of the apparatus to decrease or contaminants to be carried to the patient. State-of-the-art filters must be frequently replaced, which is time-consuming and expensive.

In accordance with the invention, it is proposed that the filters be provided with functional surfaces. This increases the service life of the filters and thus lowers costs.

On their side facing the patient, the filters are preferably antiseptic and/or self-cleaning and/or hydrophobic and/or oleophobic and/or photocatalytic. It is proposed especially that notches, webs, thickened sections, or grooves in the area in which a filter is mounted be provided with antiseptic and/or self-cleaning and/or hydrophobic and/or oleophobic and/or photocatalytic properties.

It is also proposed that points of contact between filters and the apparatus and/or points of contact between filters and the user be provided with antiseptic and/or self-cleaning and/or hydrophobic and/or oleophobic and/or photocatalytic properties. The photocatalytic properties cause adhering particles and microorganisms to be "cold-combusted".

It is preferred that the area near the end of the filter that faces the air flow be furnished with suitable smooth plastics and/or lacquered surfaces and/or coated plastics and/or surfaces with texturing on the nanometer to micrometer scale in such a way that reduced friction can be realized. It is also preferred that HME filters (heat and moisture exchange filters) be finished in such a way that they have reduced frictional resistance and/or that they are antiseptic and/or self-cleaning and/or oleophobic and/or photocatalytic.

Functional surfaces have also been found to be effective for hoses. Especially in ventilators but also in other types of medical apparatus, such as suction devices, hoses are used to convey a medium, especially in the area of a connection between the user/patient and the device. The hoses usually take the form of replaceable plug-in hoses. If a hose is not regularly cleaned and/or replaced, retained particulates, dust particles, contaminants, and microorganisms can increase the flow resistance, which causes the efficiency of the apparatus to decrease or contaminants to be carried to the patient. State-of-the-art hoses must be frequently cleaned and/or replaced, which is time-consuming and expensive. Cleaning must be performed frequently and thoroughly to eliminate contamination effectively.

In accordance with the invention, it is proposed that the hoses be provided with functional surfaces. This increases the service life of the hoses and at the same time reduces the amount of time needed to clean them, thereby reducing costs.

On their side facing the patient/user, the hoses are preferably antiseptic and/or self-cleaning and/or hydrophobic and/or oleophobic and/or photocatalytic. It is proposed especially that notches, webs, thickened sections, or grooves in the area in which a hose is mounted on the apparatus and/or connected to the patient be provided with antiseptic and/or self-cleaning and/or hydrophobic and/or oleophobic and/or photocatalytic properties.

It is also proposed that points of contact between the hose and the apparatus and/or points of contact between the hose and the user be provided with antiseptic and/or self-cleaning and/or hydrophobic and/or oleophobic and/or photocatalytic properties. The photocatalytic properties cause adhering particles and microorganisms to be "cold-combusted".

It is preferred that the area near the end of the hose that faces the air flow/medium flow be furnished with suitable smooth plastics and/or lacquered surfaces and/or coated plastics and/or surfaces with texturing on the nanometer to micrometer scale in such a way that reduced friction can be realized. It is also preferred that hoses have an electrically conductive surface.

Preferably, at least some sections of the surface of a cover or container for covering or holding a medical apparatus and/or for covering or holding accessories for a medical apparatus are provided with antiseptic properties. The surfaces of the cover or container are rendered antiseptic at least in some sections, for example, by reducing the surface adhesion. The surfaces of the cover or container are rendered antiseptic at least in some sections, for example, by causing microorganisms to be destroyed and/or their growth to be inhibited. For example, the surface of the cover or container contains biocides. At least certain sections of the surface of the cover or container preferably contain silver and/or silver-containing compounds as the active substance. In another embodiment, the surface contains an antimicrobially active polymer as the active substance.

Alternatively and/or additionally, at least certain sections of the surface of the cover or container can be rendered hydrophilic. Alternatively, at least certain sections of the surface of the cover or container can be rendered antiseptic and/or photocatalytic and/or additionally hydrophilic. At least some sections of the cover or container can have a scratch-resistant surface. The cover or container preferably has a surface that is antiseptic, self-cleaning and/or hydrophilic and/or oleophobic and/or low-friction and/or conductive.

FIG. 14 shows an example of a design of contact points 54 of the molded bodies 55 of the invention for medical apparatus. Molded bodies 55 of the invention for medical apparatus preferably have contact points 54 with antiseptic properties, at least in some areas. The contact points 54 are rendered antiseptic at least in some sections, for example, by reducing the surface adhesion. The contact points are rendered antiseptic at least in some sections, for example, by causing microorganisms to be destroyed and/or their growth to be inhibited. For example, the contact points contain biocides. At least certain sections of the contact points preferably contain silver and/or silver-containing compounds as the active substance. In another embodiment, the contact points contain an antimicrobially active polymer as the active substance.

Alternatively and/or additionally, at least certain sections of the contact points can be rendered hydrophilic. Alternatively, at least certain sections of the contact points can be rendered antiseptic and/or photocatalytic and/or additionally hydrophilic. At least some sections of a molded body can have a scratch-resistant contact point. A molded body preferably has a contact point that is antiseptic, self-cleaning and/or hydrophilic and/or oleophobic and/or low-friction and/or conductive. It is also contemplated that the contact points may have all of the properties mentioned in the text, either alone or in combination, at least in some sections.

These modified molded bodies for medical apparatus contain adhesion-reducing substances in such an amount that the adhesion of microorganisms on their surface is at least 50% lower than in the case of unmodified molded bodies, and/or they contain biocidal substances in such an amount that at least 60% of the remaining microorganisms are destroyed within 24 hours.

These modified molded bodies have adhesion-reducing substances incorporated in them. In addition, their surfaces are modified by adhesion-reducing substances.

Furthermore, biocidal substances are incorporated: silver, substances that release silver ions, copper, substances that release copper ions, zinc, or substances that release zinc ions.

To produce modified molded bodies, the adhesion-reducing and biocidal substances are introduced into the plastics.

A method for introducing, e.g., biocidal materials, into the plastics is the solvent casting method. In this method, cured plastics are ground, mixed with biocides, and compressed in the mold again, possibly under the action of heat.

The biocide can also be added during the plastic injection operation. In the case of casting materials, a biocide is added to any one of the components of the uncured casting material. The curing process then results in a rubber that has biocidal properties.

However, it can also be added during polymerization or during the crosslinking reaction. Finally, metal (e.g., silver) with zeolite in particle form can be dispersed in the polymer melt and extruded together.

Alternatively, the adhesion-reducing substances can be applied to the surface of the plastics, and the biocidal substances can be incorporated in the plastics.

These combinations of antiadhesive function and microbiocidal activity are especially advantageous. They result in a new type of microbiocidal surface with the following properties:
- coatings with low surface energy
- very smooth surfaces
- bacteria do not adhere and do not grow
- microbiocidal surfaces with coatings that contain germicidal components.

In accordance with the invention, at least some sections of a molded body of an oxygen supply valve and/or humidifier and/or ventilator and/or patient interface and/or head fastening device and/or hose and/or accessory part has at least one property of the invention that is imparted via the surface.

The invention claimed is:

1. A molded body, wherein the molded body is a protruding edge for a face mask and is made of plastic material, and wherein a surface of the molded body comprises elevations formed by particles fixed on at least one or more portions of the surface.

2. The molded body of claim 1, wherein the protruding edge is configured for resting on a patient's face.

3. The molded body of claim 1, wherein the plastic material comprises one or more polymers selected from the group consisting of polyethylene, polypropylene, polyvinyl chloride, polystyrene, polycarbonate, cellophane, cellulose acetate, polyolefins, fluorocarbon resins, polyhydroxyethyl methacrylate, polymethyl methacrylate, polysiloxanes, polyethers, polyesters, polyacetals, polyvinyls, polyethersilicones, polyurethanes, natural and synthetic rubber, silicone, latex, ABS resin, acrylic resins, triacetates, vinylides, and rayon.

4. The molded body of claim 1, wherein the plastic material comprises silicone.

5. The molded body of claim 1, wherein the molded body is injection molded.

6. The molded body of claim 1, wherein the particles comprise particles selected from the group consisting of silicates, minerals, metal oxides, mixed-metal oxides, metal powders, silicic acids, pigments, and polymers.

7. The molded body of claim 6, wherein the particles comprise silicates.

8. The molded body of claim 1, wherein the particles have hydrophobic properties.

9. The molded body of claim 1, wherein the particles are fixed to the at least one or more portions of the surface by a polymeric matrix.

10. The molded body of claim 9, wherein the polymeric matrix comprises at least one thermoplastic, elastomeric, or thermosetting material.

11. The molded body of claim 1, wherein the particles comprise antiseptic particles.

12. The molded body of claim 1, wherein the particles comprise hydrophobic particles having a diameter of from 0.02 µm to 100 µm.

13. The molded body of claim 1, wherein the particles comprise particles with antimicrobial properties having a diameter of from 0.05 to 2,000 nm.

14. The molded body of claim 1, wherein the particles comprise microparticles having a diameter of from 0.02 µm to 100 µm.

15. The molded body of claim 14, wherein the microparticles have a diameter of from 0.1 µm to 50 µm.

16. The molded body of claim 14, wherein the microparticles have a diameter of from 0.1 µm to 10 µm.

17. The molded body of claim 1, wherein the particles have been applied to the at least one or more portions of the surface of the molded body in a solvent by one or more of spraying, doctor blade coating, dropping or immersing.

18. The molded body of claim 1, wherein the particles have been applied to the at least one or more portions of the surface of the molded body by pressing them onto the at least one or more portions.

19. The molded body of claim 1, wherein the particles have been applied to the at least one or more portions of the surface of the molded body by providing a mold with the particles before injection molding and pressing the particles onto the at least one or more portions during the injection molding.

20. The molded body of claim 1, wherein the elevations have heights of from 5 nm to 200 µm.

21. The molded body of claim 20, wherein the elevations are separated by a distance of from 5 nm to 200 µm.

22. The molded body of claim 1, wherein the elevations have heights of from 20 nm to 25 µm.

23. The molded body of claim 22, wherein the elevations are separated by a distance of from 20 nm to 25 µm.

24. The molded body of claim 1, wherein the elevations have heights of from 50 nm to 4 μm.

25. The molded body of claim 24, wherein the elevations are separated by a distance of from 50 nm to 4 μm.

26. The molded body of claim 1, wherein at least a portion or section of the surface of the molded body has a surface energy of less than 35 mN/m.

27. A molded body, wherein the molded body is a protruding edge for a face mask, is made of one or more polymers selected from the group consisting of polyethylene, polypropylene, polyvinyl chloride, polystyrene, polycarbonate, cellophane, cellulose acetate, polyolefins, fluorocarbon resins, polyhydroxyethyl methacrylate, polymethyl methacrylate, polysiloxanes, polyethers, polyesters, polyacetals, polyvinyls, polyethersilicones, polyurethanes, natural and synthetic rubber, silicone, latex, ABS resin, acrylic resins, triacetates, vinylides, and rayon, and wherein at least one or more portions of a surface of the molded body comprise elevations formed by particles which comprise particles selected from the group consisting of silicates, minerals, metal oxides, mixed-metal oxides, metal powders, silicic acids, pigments, and polymers.

28. The molded body of claim 27, wherein the one or more polymers comprise silicone.

29. The molded body of claim 28, wherein the particles comprise silicates.

30. The molded body of claim 27, wherein the particles are fixed to the at least one or more portions of the surface by a polymeric matrix.

31. The molded body of claim 30, wherein the polymeric matrix comprises at least one thermoplastic, elastomeric, or thermosetting material.

32. The molded body of claim 27, wherein the particles have been applied to the at least one or more portions of the surface of the molded body in a solvent by one or more of spraying, doctor blade coating, dropping or immersing.

33. The molded body of claim 27, wherein the particles have been applied to the at least one or more portions of the surface of the molded body by pressing them onto the at least one or more portions.

34. The molded body of claim 27, wherein the particles have been applied to the at least one or more portions of the surface of the molded body by providing a mold with the particles before injection molding and pressing the particles onto the at least one or more portions during the injection molding.

35. The molded body of claim 27, wherein the elevations have heights of from 5 nm to 200 μm.

36. The molded body of claim 35, wherein the elevations are separated by a distance of from 5 nm to 200 μm.

37. The molded body of claim 27, wherein the elevations have heights of from 20 nm to 25 μm.

38. The molded body of claim 37, wherein the elevations are separated by a distance of from 20 nm to 25 μm.

39. The molded body of claim 27, wherein the elevations have heights of from 50 nm to 4 μm.

40. The molded body of claim 39, wherein the elevations are separated by a distance of from 50 nm to 4 μm.

41. The molded body of claim 27, wherein at least a portion or section of the surface of the molded body has a surface energy of less than 35 mN/m.

42. A molded body, wherein the molded body is a protruding edge for a face mask, is made of silicone in at least one or more sections thereof, and has a surface at least one or more portions of which comprise elevations formed by particles which comprise particles selected from the group consisting of silicates, minerals, metal oxides, mixed-metal oxides, metal powders, silicic acids, pigments, and polymers.

43. The molded body of claim 42, wherein the particles comprise silicates.

44. The molded body of claim 42, wherein the particles are fixed to the at least one or more portions of the surface by a polymeric matrix.

45. The molded body of claim 44, wherein the polymeric matrix comprises at least one thermoplastic, elastomeric, or thermosetting material.

46. The molded body of claim 43, wherein the particles are fixed to the at least one or more portions of the surface by a polymeric matrix.

47. The molded body of claim 46, wherein the polymeric matrix comprises at least one thermoplastic, elastomeric, or thermoplastic material.

48. The molded body of claim 42, wherein the particles have been applied to the at least one or more portions of the surface of the molded body in a solvent by one or more of spraying, doctor blade coating, dropping or immersing.

49. The molded body of claim 42, wherein the particles have been applied to the at least one or more portions of the surface of the molded body by pressing them onto the at least one or more portions.

50. The molded body of claim 42, wherein the particles have been applied to the at least one or more portions of the surface of the molded body by providing a mold with the particles before injection molding and pressing the particles onto the at least one or more portions during the injection molding.

51. The molded body of claim 42, wherein the elevations have heights of from 5 nm to 200 μm.

52. The molded body of claim 51, wherein the elevations are separated by a distance of from 5 nm to 200 μm.

53. The molded body of claim 42, wherein the elevations have heights of from 20 nm to 25 μm.

54. The molded body of claim 53, wherein the elevations are separated by a distance of from 20 nm to 25 μm.

55. The molded body of claim 42, wherein the elevations have heights of from 50 nm to 4 μm.

56. The molded body of claim 55, wherein the elevations are separated by a distance of from 50 nm to 4 μm.

57. The molded body of claim 42, wherein at least a portion or section of the surface of the molded body has a surface energy of less than 35 mN/m.

58. A method of producing the molded body of claim 1, wherein the method comprises injection molding of plastic material to form a protruding edge of a face mask that is configured for resting on a patient's face, and providing at least one or more portions of a surface of the protruding edge with particles to form elevations on the one or more portions of the surface.

59. The method of claim 58, wherein the particles are fixed to the at least one or more portions of the surface by a polymeric matrix.

60. The method of claim 59, wherein the polymeric matrix comprises at least one thermoplastic, elastomeric, or thermosetting material.

61. The method of claim 58, wherein the plastic material comprises one or more polymers selected from the group consisting of polyethylene, polypropylene, polyvinyl chloride, polystyrene, polycarbonate, cellophane, cellulose acetate, polyolefins, fluorocarbon resins, polyhydroxyethyl methacrylate, polymethyl methacrylate, polysiloxanes, polyethers, polyesters, polyacetals, polyvinyls, polyethersilicones, polyurethanes, natural and synthetic rubber, silicone, latex, ABS resin, acrylic resins, triacetates, vinylides, and rayon.

62. The method of claim 58, wherein the plastic material comprises silicone.

63. The method of claim 58, wherein the particles comprise particles selected from the group consisting of silicates, minerals, metal oxides, mixed-metal oxides, metal powders, silicic acids, pigments, and polymers.

64. The method of claim 58, wherein the particles comprise silicates.

65. The method of claim 58, wherein the particles are applied to the at least one or more portions of the surface of the molded body in a solvent by one or more of spraying, doctor blade coating, dropping or immersing.

66. The method of claim 58, wherein the particles are applied to the at least one or more portions of the surface of the molded body by pressing them onto the at least one or more portions.

67. The method of claim 58, wherein the particles have been applied to the at least one or more portions of the surface of the molded body by providing a mold with the particles before injection molding and pressing the particles onto the at least one or more portions during the injection molding.

* * * * *